(12) United States Patent
Gandy et al.

(10) Patent No.: US 9,439,949 B2
(45) Date of Patent: Sep. 13, 2016

(54) DECELLULARIZATION AND RECELLULARIZATION OF DONOR TISSUES FOR MINIMIZED OR OBVIATED REJECTION REACTIONS

(71) Applicants: James Bennie Gandy, West Monroe, LA (US); Jeri Gandy, West Monroe, LA (US)

(72) Inventors: James Bennie Gandy, West Monroe, LA (US); Jeri Gandy, West Monroe, LA (US)

(73) Assignee: Gray Reed & McGraw, P.C., Houston, TX (US)

( * ) Notice: Subject to any disclaimer, the term of this patent is extended or adjusted under 35 U.S.C. 154(b) by 0 days.

(21) Appl. No.: 14/073,729

(22) Filed: Nov. 6, 2013

(65) Prior Publication Data

US 2014/0377226 A1    Dec. 25, 2014

Related U.S. Application Data

(60) Provisional application No. 61/723,691, filed on Nov. 7, 2012, provisional application No. 61/842,280, filed on Jul. 2, 2013.

(51) Int. Cl.
*A61K 38/19* (2006.01)
*A61K 35/28* (2015.01)
*A61K 35/22* (2015.01)
*A61K 38/18* (2006.01)
*A61K 35/12* (2015.01)

(52) U.S. Cl.
CPC ............... *A61K 38/19* (2013.01); *A61K 35/22* (2013.01); *A61K 35/28* (2013.01); *A61K 38/1858* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 6,376,244 B1 * | 4/2002 | Atala | 435/376 |
| 8,734,854 B2 * | 5/2014 | Gandy et al. | 424/529 |
| 2010/0093066 A1 * | 4/2010 | Taylor et al. | 435/284.1 |
| 2012/0064537 A1 * | 3/2012 | Ross | 435/6.13 |

* cited by examiner

*Primary Examiner* — Allison Fox
(74) *Attorney, Agent, or Firm* — David G. Henry

(57) ABSTRACT

The method of tissue transplantation involving recellularizing of a donor organ with the utilization of the recipient's cytokines collected from the recipient's blood plasma at less than systemic pressure, and at the temperature greater than freezing and less than normal systemic temperature of the recipient's blood. Specifically, a method of harvesting a platelet-derived growth factors from platelet rich plasma (PRP), the growth factors having increased weight.

17 Claims, No Drawings

DECELLULARIZATION AND RECELLULARIZATION OF DONOR TISSUES FOR MINIMIZED OR OBVIATED REJECTION REACTIONS

PRIORITY CLAIM

Applicants and inventors claim priority, pursuant to 35 U.S.C. §119(e), with respect to U.S. Provisional Patent Applications Nos. 61/723,691, filed 7 Nov. 2012 and 61/842,280, filed 2 Jul. 2013.

BACKGROUND INFORMATION

According to United States Government statistics, a person is added to an organ transplant waiting list every 10 minutes. Each day, an average of 79 people receive organ transplants. However, an average of 18 people die each day waiting for transplants that can't take place because of the shortage of donated organs.

One particular topic of pertinence to the present invention is that of kidney disease. It is reported that, in 2009, $42.5 billion was spent in the U.S. for support of some 400,000 dialysis patients and 172,000 transplant recipients. Medicare paid 68 percent of that bill.

Successful kidney transplant procedures, from a financial standpoint, produced a break-even point in only three years, with over 85% of all kidney transplant recipients surviving at least five years (while less than 36% of dialysis patients survive that long). Also during 2009, some 49,000 people died of kidney failure—most for lack of available kidneys for transplant.

As our population ages, and fewer, healthy organ donors are available, it is reasonable to assume that organ shortages, and deaths from unfulfilled organ needs will only rise. Whether already the product of the aging populating, or for one or more other reason(s), the number of persons in need or organ transplants is rising at a much faster pace than the supply of donated organs. Absent a heretofore unforeseen breakthrough in medical science, the picture is bleak indeed for those presently on transplant waiting lists, as even more so for ever-increasing portions of future such persons.

SUMMARY OF THE PRESENT INVENTION

The present inventors have, for the first time, successfully transplanted a kidney from an animal of one species into one of a different species. The kidney is functioning normally, and no rejection occurred.

The implications of this achievement cannot be overstated. Having, for the first time, a nearly endless supply of donor organs (even if only considering kidneys—the organs involved in the present inventors' initial work) will save tens of thousands of lives, and will collectively save society billions of dollars.

DETAILED DESCRIPTION OF ONE IMPLEMENTATION OF THE PRESENT INVENTION

A kidney was removed from a donor animal (a pig) and was later transplanted into a recipient animal (another, non-familial pig). The procedure produced a functioning kidney (actively producing urine) in the recipient, without rejection or the formation of scar tissue after two weeks post-transplantation.

The procedure involves decellularization of the donor organ, followed by the newly developed procedures of the present invention for recellularizing the donor organ with cells grown from the recipient's stem cells through use of cytokines, or "growth factors", that are extracted in a novel and unobvious manner from the recipient's blood plasma. It is presently believed that the use of cytokines, extracted in the manner described below, is responsible for this first-ever rejection-free and functional organ transplantation between non-tissue matching organisms.

The process for adapting a donor organ for implantation into a recipient (even of a different species, provided that structural impediments are lacking) is described as follows:

The donor organ is decellularized using distilled water and 10% SDS (sodium dodecyl sulfate). For a pig kidney, decellularization was conducted for a period of approximately 18 hours. Decellularization is best done after a freeze-thaw cycle, as known in the art (begins the process of rupturing cell membranes), and uses a peristaltic pump (set on low volume).

The kidney (or other organ) is immersed in decellularization medium during process, with medium being recirculated, but with medium being exchanged for new medium approximately every 4 hours, for a total decellularization time of between approximately 16 and 18 hours. This process is carried out at a "cold" temperature (above, but near freezing level).

After decellularization, the organ is flushed with distilled water to remove decellularization medium, and antibiotics are infused to insure that the decellularized organ is non-microbial.

Cell culture (Dulbecco's Eagle Medium) is next circulated through the organ through same pump and circuit as during decellularization, to which is added stem cells harvested from bone marrow of the intended recipient as well as cytokines harvested from blood of the recipient. The stem cells and cytokines are introduced at approximately 6-8 hour increments (between 5 and 10 ml injections). Recellularization pretransplantation occurs over approximately 36 to 48 hours, through the organ's arterial to venous circuit.

As will be described below in considerable detail, a very important feature of practice of the present invention relates to the use of a particular state or kind of cytokines ("growth factors") that are to be used in the process of recellularizing the to-be-implanted organ. One method involves collecting growth factors from plasma from blood that has rested (optimally) at "room temperature" (less than systemic temperature, but above freezing level) and at less than systemic pressure (ambient pressure or less) for approximately two days. This successfully produces the type of (state of) growth factors that are essential for practice of the present method. However, another method, presently believed to be optimal for extracting cytokines (also known as "growth factors") suitable for the present method involves extraction from platelet rich plasma ("PRP") and the use of a vacuum.

Through this latter, optimal method, PRP is obtained, and placed under a vacuum, preferably under a sub-atmospheric or negative pressure. The PRP is in an unfrozen state, preferably at room temperature. Similarly, the vacuum is applied at above freezing, more preferably at room temperature conditions.

In accordance with the present invention, the PRP is placed in one or more vials. A vacuum is applied using a conventional vacuum pump, wherein the platelet rich plasma product is placed in a separate vacuum chamber. The vacuum pump is operated to apply a negative pressure to the PRP. The vacuum is applied preferably at temperatures above freezing. In one example, it is applied between 1° C. and 37° C. and at a sub-atmospheric, negative pressure, preferably between 5 millibars and 1 atmosphere. As a result of the application of the negative pressure, the cytokines are released into the surrounding nondestructive medium.

There is a direct inverted correlation between time versus vacuum pressure. The shorter the length of time the vacuum is applied, the higher the vacuum pressure must be. Conversely, the longer the length of time the vacuum is applied, the lower the vacuum pressure needs to be to release the growth factors from the platelets. A vacuum source suitable for use in the process of the present invention is a rotary vane direct drive vacuum pump commercially available from Labconco Corporation of Kansas City, Mo. It should be understood that other commercially available vacuum generating devices are operable for use in the present invention.

As a result of the vacuum process, the cytokines are separated or released from the platelets in the growth factor starting material into the plasma, leaving the platelets intact. The negative pressure created by the vacuum pulls the growth factors out of the platelets and into the plasma. The separated growth factors are mixed with a medium that is not destructive to the growth factors in a bioactive state to promote tissue growth (recellularization of a to-be-implanted organ).

In one example of the process of the present invention, analysis of the vacuumed plasma using light microscopy and alpha granule staining techniques revealed intact platelets devoid of alpha granules in addition to the presence of platelet derived growth factors (PDGF) distributed in the plasma.

By way of explanation of one feature of the present invention: There are two types of presently-known kinds (or states) of PDGF. One can use PDGF as a marker. PDGF normally weighs approximately 16 to 32 K Dalton. This form of PDGF exist as a natural healing process that is triggered by normal cell activation. Unfortunately, the healing process effected by such growth factors is also responsible for the formation of scar tissue (necessary for many healing processes, such as of wounds that require rapid tissue "bandaging"). While desirable (if not necessary) in healing many processes, scar formation in an organ recellularization process is a fatal byproduct, as a number of researchers who have failed in attempts to successfully recellularize organs for transplantations have discovered, in part, through use of conventionally produced, lower-weight, "activated" growth factors.

In great contrast, growth factors extracted from the platelets in accordance with practicing the present invention were measured to have an increased weight of 70-76 kDaltons. The kind of (or "non-activated" state of) cytokines that are produced as described herein are conducive to the natural tissue-building processes that are essential to any successful recellularization of an organ for transplantation. Use of such "non-activated" growth factors appears elemental to the success of the present method.

As alluded to above, the 76 and 130 K Dalton weight form of PDGF is in a non-activated form or state, and is believed to be involved in tissue-building, at least in some non-traumatic contexts (including fetal development). Tissue construction effected through use of these non-trauma-activated growth factors tend to be "normal" tissues. Therefore, use of these latter, heavier, "non-trauma-activated" cytokines are believed to enable recellularization of the donor organ, without the destructive scar formation that has met all prior attempts to successfully achieve organ recellularization with a functional end product.

Use of the higher-weight, "non-activated" cytokines harvested as described above, and in practicing the present invention (as contrasted to use of cytokines/growth factors used by others who have failed to achieve the results here reported) lie at the heart of success in practice of the present invention in producing at least a rejection-resistant and functional organ for transplant, into a non-tissue-matching donee, and even in a xenotransplantation (cross species) context. Conventionally-harvested growth factors, when used in attempts to recellularize organs, produced non-functional scar tissue, resulting in utter failure of attempts at results now achieved by the present inventors.

After no more than approximately 48 hours, recellularization, using stems cells and growth factors as described above, reaches a level such that the organ can be implanted into a recipient with adequate cellular foundation for maturation into a normally functioning organ, and approximately 10 days post implantation will produce a fully redeveloped and functioning organ. Immediately after implantation, the recipient receives low dose heparin injections to prevent any clotting during continued organ development in vivo. Recellularization in vivo is another unique feature of the present invention (not before attempted by any known researcher), and is believed also to play a role in the formation, not of dysfunctional scar tissue in the newly cellularized organ, but of functioning, healthy tissue that is, in effect, the donee's own. Tissue growth effected in vivo by the growth factors harvested as described as prescribed above continues as desired, because, in vivo, the growth factors remain in the non-scar-building state, and instead effect the construction of the desired, healthy, functioning tissues of the organ and, in turn, a fully-functioning organ that the recipient's body "sees" as its own.

Post-implantation, the recipient is injected daily for approximately 10 days (1 to 2 ml each injection, thus far) after implantation with autologous plasma to promote continued cellular population of the transplanted organ. This, it is believed, promotes further stem cell production and mitosis of resulting cells that form into the organ's needed, specific cell types. Efficacious injections thus far have been sub-coetaneous, but IM may also prove to be effective.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A method for adapting tissue for trans-organism implantation comprising the steps of:
    selecting donor tissue from a first organism;
    decellularizing said donor tissue;
    selecting stem cells and cytokines from a second organism, said cytokines being extracted from said second organism's blood, at least in part when such blood is at less than systemic pressure; and
    infusing said donor tissue with said stem cells and said cytokines.

2. The method of claim 1 wherein said donor tissue is an organ.

3. The method of claim 2 wherein said donor tissue is a kidney.

4. The method of claim 1 wherein said cytokines being extracted is performed when said blood of said second organism is at a pressure less than ambient pressure.

5. The method of claim 1 wherein said cytokines being extracted is performed when said blood of said second organism is at a temperature greater than freezing and less than normal systemic temperature of said second organism.

6. The method of claim 1 further comprising the step of implanting said donor tissue, after said infusing, into said second organism.

7. The method of claim 6, further comprising a step of infusing said donor tissue with a second measure of said stem cells and a second measure of said cytokines, after said implanting.

8. The method of claim 6, further comprising the step of infusing said donor tissue with autologous plasma, after said implanting.

9. The method of claim 1, wherein said first organism and said second organism are different species.

10. The method of claim 9 wherein said donor tissue is an organ.

11. The method of claim 10 wherein said donor tissue is a kidney.

12. Modified tissue for trans-organism implantation by the method of any one of claim 1, 6, 4, 5, 7, or 8.

13. The modified tissue of claim 12 wherein said donor tissue is an organ.

14. The modified tissue of claim 13 wherein said donor tissue is a kidney.

15. The Modified tissue of claim 12 wherein said donor tissue is from a first species and said cells and cytokines are from a second species.

16. The modified tissue of claim 15 wherein said donor tissue is an organ.

17. The modified tissue of claim 16 wherein said donor tissue is a kidney.

* * * * *